(12) United States Patent
Arai et al.

(10) Patent No.: US 7,416,527 B2
(45) Date of Patent: Aug. 26, 2008

(54) INSTRUMENT FOR CORONARY ARTERY BYPASS GRAFT SURGERY

(75) Inventors: Hirokuni Arai, Tokyo (JP); Akira Kawamata, Akita (JP); Hideaki Asai, Akita (JP); Haruhiko Masuda, Akita (JP)

(73) Assignee: Sumitomo Bakelite Co. Ltd. (JP)

( * ) Notice: Subject to any disclaimer, the term of this patent is extended or adjusted under 35 U.S.C. 154(b) by 409 days.

(21) Appl. No.: 10/913,016

(22) Filed: Aug. 6, 2004

(65) Prior Publication Data

US 2005/0049463 A1    Mar. 3, 2005

(30) Foreign Application Priority Data

| | | |
|---|---|---|
| Aug. 8, 2003 | (JP) | 2003-290095 |
| Nov. 5, 2003 | (JP) | 2003-375888 |
| Jan. 27, 2004 | (JP) | 2004-018082 |
| Aug. 3, 2004 | (JP) | 2004-227197 |

(51) Int. Cl.
*A61F 2/00* (2006.01)

(52) U.S. Cl. ..................................... 600/37

(58) Field of Classification Search ......... 128/897–899; 600/37, 201–210, 215, 216, 16–17; 601/6–14; 606/1, 108, 191
See application file for complete search history.

(56) References Cited

U.S. PATENT DOCUMENTS

| | | | |
|---|---|---|---|
| 5,836,311 A | | 11/1998 | Borst et al. |
| 6,015,378 A | * | 1/2000 | Borst et al. ............... 600/37 |
| 6,019,722 A | * | 2/2000 | Spence et al. ............. 600/210 |
| 6,517,563 B1 | * | 2/2003 | Paolitto et al. ............ 606/205 |
| 2003/0009080 A1 | * | 1/2003 | Peng et al. ................ 600/37 |
| 2003/0078470 A1 | * | 4/2003 | Borst et al. ............... 600/37 |
| 2004/0260209 A1 | * | 12/2004 | Ella et al. ................. 601/7 |

FOREIGN PATENT DOCUMENTS

WO    WO 02/054937 A2    7/2002

* cited by examiner

*Primary Examiner*—Charles A. Marmor, II
*Assistant Examiner*—Christine D Hopkins
(74) *Attorney, Agent, or Firm*—Smith, Gambrell & Russell

(57) ABSTRACT

An instrument for coronary artery bypass graft surgery has at least three sets of suction units, respectively provided with a flexible tube; a suction head disposed at an end portion of the flexible tube; a three-way cock mounted on the flexible tube; and a retainer which retains the flexible tube.

11 Claims, 5 Drawing Sheets

109

INSTRUMENT FOR CORONARY ARTERY BYPASS GRAFT SURGERY

This application is based on Japanese patent application NO.2003-290095, Japanese patent application NO.2003-375888, Japanese patent application NO.2004-018082, and Japanese patent application NO.2004-227197, the contents of which are incorporated hereinto by reference.

BACKGROUND OF THE INVENTION

1. Field of the Invention

The present invention relates to an instrument for coronary artery bypass graft surgery.

2. Description of the Related Art

In recent years, catheter intervention for a patient suffering from an ischemic heart disease such as myocardial infarction has rapidly come to be popularly performed. Typical methods of the catheter intervention include coronary artery angiodilatation and intravascular stenting, both of which have the advantage of being minimally invasive to a patient, and of requiring only a short stay in a hospital.

On the other hand, for a patient to whom the catheter treatment is not applicable, coronary artery bypass graft (hereinafter simply referred to as CABG) is well known as an effective method. The CABG is an operation of anastomosing an end of a graft vessel detached from for example an internal thoracic artery or gastroepiploic artery, to a peripheral side of the coronary artery suffering stenosis, which is the cause of ischemia, to thereby resolve the ischemia.

Many of the patients who need to undergo the CABG have obstruction or stenosis in a plurality of coronary arteries, calcification in ascending aorta, or a chronic disease in the brain, kidney or a respiratory organ, and are senior aged. Accordingly, a risk originating from the CABG on the part of such patients is far from low. Especially, a riskiest procedure to the patient is extracorporeal circulation, to be performed with a heart lung machine while the patient's heartbeat is stopped. Applying a heart lung machine to a patient suffering from progressed arteriosclerosis is exactly like supplying high-pressure water through a rusted pipe. In other words, substances deposited inside the blood vessel may be swept away and thus obstruct another blood vessel, thereby inducing a complication such as cerebral infarction or the like.

For this type of patients, a procedure of anostomosing a bypass graft while the heart is beating without using a heart lung machine has lately been attempted, and has been achieving excellent results. Such procedure is called "off-pump coronary artery bypass" (hereinafter referred to as OPCAB).

A drawback of the OPCAB is that a lot of skill is required for performing an anastomosis to perfection in a short time, since the patient's heart keeps beating during the operation. In the event that an anastomosis has been imperfectly performed, a blood clot may be formed in an area including the anastomosed point, the coronary artery and the graft vessel, to thereby cause obstruction. This problem, however, has been solved by utilizing a stabilizer, which restrains a motion of the part to be anastomosed, thereby facilitating an anastomosis of the graft vessel under a stabilized state. As a result, because of improvement in precision of anastomosis, outcome of the OPCAB procedure has shown a dramatic improvement (U.S. Pat. No. 5,836,311 Specifications).

Further, the international patent application whose publication number is WO02/054937 discloses a device for holding the heart by a suction pressure to adjust a position of thereof, to improve precision of anastomosis of an affected part that cannot be brought into view under a normal heart orientation and is hence difficult to perform an anastomosis. The device disclosed in the international patent application is provided with a suction pad capable of adsorbing to a heart wall surface, an arm for adjusting a position of the suction pad, and a vacuum tube communicated with the suction pad and connectable to a vacuum source. However, this device utilizes a force in only one direction to adjust a position of the heart. Accordingly, the heart may shift from an appropriate position or even fall off from the device, during an anastomosis procedure with the heart held in a certain position.

SUMMARY OF THE INVENTION

The present invention has been conceived in view of the foregoing situation, with an object to provide a instrument for coronary artery bypass graft surgery that can adjust a position of a heart preventing the heart from shifting its position or falling off from the instrument, when handling an affected part that is difficult to perform an anastomosis in an off-pump coronary artery anastomosis, thereby facilitating a safe anastomosis.

According to the present invention, there is provided a instrument for coronary artery bypass graft surgery comprising multiple sets of suction units, respectively provided with a flexible tube; a suction head disposed at an end portion of the flexible tube; a switchgear mounted on the flexible tube; and a retainer which retains the flexible tube.

A purpose of the instrument for coronary artery bypass graft surgery according to the present invention is to retain a heart at a desired position. According to the present invention, the instrument for coronary artery bypass graft surgery is provided with multiple suction heads. Therefore, the surgical instrument can retain a heart from plurality of directions. Also, since multiple suction heads are provided, the surgical instrument can securely retain a heart at a desired position. As a result, an anastomosis can be safely performed in a coronary artery bypass grafting.

In the instrument for coronary artery bypass graft surgery according to the present invention, at least three sets of suction units may be provided. Such structure can more securely retain a heart at a desired position. As a result, an anastomosis can be more safely performed in a coronary artery bypass grafting.

In the instrument for coronary artery bypass graft surgery according to the present invention, a connector may be provided between the suction head and the flexible tube, such that the connector allows one of the suction head and the flexible tube to relatively move with respect to the other. Such structure increases motion freedom of the suction units on positioning the heart. As a result, a position of the heart can be more precisely adjusted.

In the instrument for coronary artery bypass graft surgery according to the present invention, the connector may be provided with a bellows tube communicating with the flexible tube. Such structure further ensures a relative movement of one of the suction head and the flexible tube with respect to the other.

In the instrument for coronary artery bypass graft surgery according to the present invention, an angular motion range of the flexible tube with respect to the suction head may be not less than 30 degrees to not more than 180 degrees, in a horizontal plane parallel to a sticking area of the suction head. Also, in the instrument for coronary artery bypass graft surgery according to the present invention, an angular motion range of the flexible tube with respect to the suction head may be not less than 30 degrees to not more than 180 degrees, in a vertical plane perpendicular to a sticking area of the suction head. Such configuration permits adjusting a position of a heart at the same time as retaining the heart at a desired position. Meanwhile, the angular motion range herein stands for a range of angles in which the flexible tube can move with respect to the suction head.

In the instrument for coronary artery bypass graft surgery according to the present invention, the suction head may be provided with an opening on its sticking area, and the opening may have a plurality of slit-like grooves formed on an inner surface thereof. Such configuration further minimizes a risk that the heart shifts its position or falls off from the surgical instrument. Also, according to the present invention, the plurality of grooves may be provided in a substantially orthogonal direction with respect to the sticking area (i.e. along a direction of the suction) and substantially parallel to one another.

In the instrument for coronary artery bypass graft surgery according to the present invention, an end portion of the suction head may be made softer than an inner portion of the suction head. Such structure permits more secure attachment of the suction head to a heart.

In the instrument for coronary artery bypass graft surgery according to the present invention, the flexible tube may include a main tube, a branch section communicating with the main tube, and a plurality of sub tubes respectively communicating with the branch section, such that a plurality of the suction heads are respectively disposed on the different sub tubes. Such structure permits miniaturization of the surgical instrument as a whole, as well as improvement of controllability of the suction unit.

In the instrument for coronary artery bypass graft surgery according to the present invention, the three or more sub tubes may be provided.

In the instrument for coronary artery bypass graft surgery according to the present invention, a plurality of the suction heads may be connected to a single suction source via the flexible tube. Such structure permits further miniaturization of the surgical instrument as a whole. Also, since the multiple suction units can be controlled with a single suction source, work efficiency in the surgical procedure can be improved.

In the instrument for coronary artery bypass graft surgery according to the present invention, the three or more suction heads may be connected to the single suction source via the flexible tube.

Accordingly, the present invention provides the instrument for coronary artery bypass graft surgery having at the multiple suction units that can adjust a position of a heart preventing the heart from shifting its position or falling off from the instrument, when handling an affected part that is difficult to perform an anastomosis in an off-pump coronary artery anastomosis, thereby facilitating a safe anastomosis.

It is to be noted that any arbitrary combination of the above-described structural components, and expressions changed between a method and an apparatus are all effective as and encompassed by the present embodiments.

Moreover, this summary of the invention does not necessarily describe all necessary features so that the invention may also be sub-combination of these described features.

DESCRIPTION OF THE PREFERRED EMBODIMENTS

The invention will now be described based on preferred embodiments which do not intend to limit the scope of the present invention but exemplify the invention. All of the features and the combinations thereof described in the embodiment are not necessarily essential to the invention.

Referring to the accompanying drawings, embodiments of the present invention will be described hereunder. Here, constituents employed in common are given an identical numeral in all the drawings, and detailed description of such constituents may not be represented as the case may be in the subsequent passages.

An instrument for coronary artery bypass graft surgery described below is an instrument to retain a heart at a desired position. This instrument can be appropriately employed for performing a predetermined procedure to a heart, for example a coronary artery bypass grafting.

Figure 1:
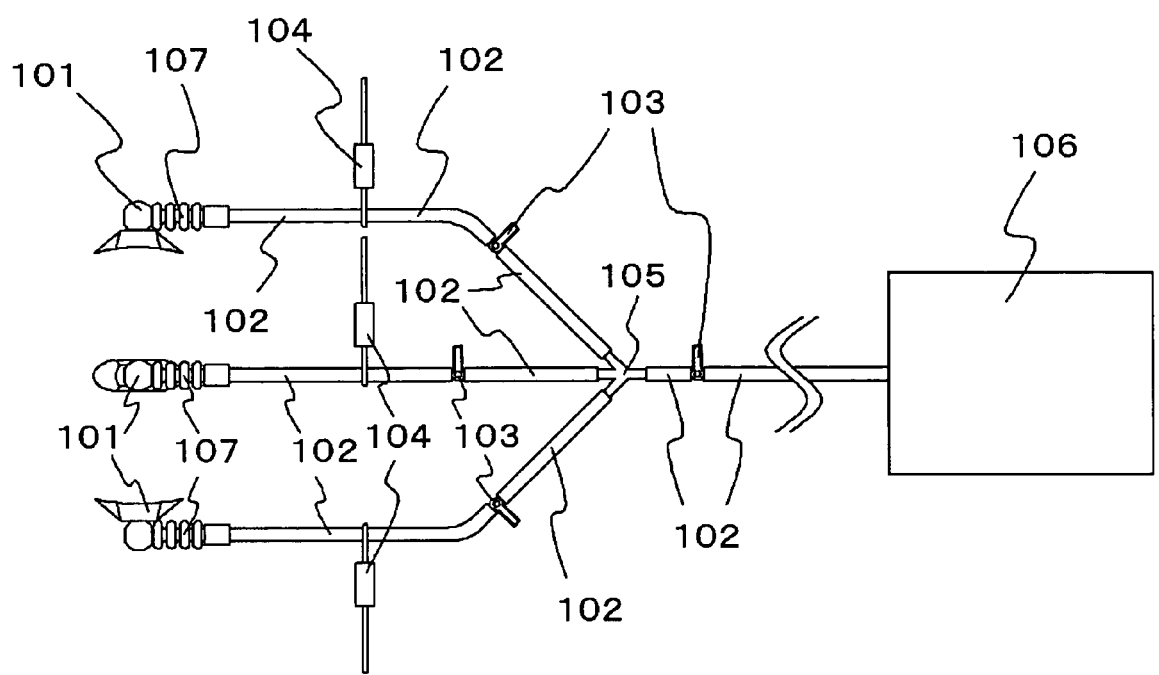
FIG. 1 is a schematic drawing showing a configuration of an instrument for coronary artery bypass graft surgery according to an embodiment of the present invention.

FIG. 1 shows an example of an instrument for coronary artery bypass graft surgery according to the present invention. The instrument for coronary artery bypass graft surgery shown in FIG. 1 is provided with multiple, three or more in FIG. 1, sets of suction units. Each of the suction units is provided with a flexible tube 102, a suction head 101 disposed at an end portion of the flexible tube 102, a three-way cock 103 serving as a switchgear mounted on the flexible tube 102, and a retainer 104 which retains the flexible tube 102.

In the instrument for coronary artery bypass graft surgery shown in FIG. 1, the flexible tube 102 includes a main tube, a three-way joint 105 which is a branch section communicating with the main tube, and three sub tubes communicating with the three-way joint 105, such that each of the three suction units have a different sub tube. In other words, the sub tubes respectively constituting different suction units are mutually connected via the three-way joint 105. Also, the other end portion of the flexible tube 102, in other words, an end portion of the main tube is connected to a suction source 106. Thus, the three suction heads 101 are connected to a single suction source 106 via the flexible tube 102. The suction source 106 may be constituted, for example, of a decompression pump.

The flexible tube 102 may be constituted of a polyurethane resin, a soft vinyl chloride resin, a silicone resin and the like. Also, the flexible tube 102 may be formed, for example, by extrusion molding. Further, the flexible tube 102 may be reinforced with a reinforcing material such as a metal coil. This prevents suspension of suction because of a kink. Accordingly, kink resistance of the flexible tube 102 is increased.

In the instrument for coronary artery bypass graft surgery shown in FIG. 1, the suction head 101 is disposed at an end portion of the flexible tube 102. To be more detailed, as already described, each of the three suction heads 101 is connected to an end portion of each of the three sub tubes branching out from a single main tube. The suction head 101 is aspirated by the suction source 106 via the flexible tube 102, to be thereby stuck to a surface of an object.

Here, the object to be stuck to is a heart. Accordingly, the suction head 101 is preferably constituted of a material that achieves intimate contact with a heart wall surface. The suction head 101 may be for example constituted of an elastic material. Such constitution permits the suction head 101 to adequately fit a heart wall surface, thus to secure sufficient adherence. To cite a few examples, a silicone resin, a styrene-ethylene-butadiene-styrene resin, an elastomer such as a urethane elastomer and the like may be preferably employed to constitute the suction head 101.

The suction head 101 may have a pad-like shape. Also, the suction head 101 may be formed in a circular shape in a plan view. Alternatively, a form of the suction head 101 may be substantially oval as shown in FIG. 1. Forming the suction head 101 in an oval shape permits the suction head 101 to stick to a heart wall surface over a maximal area, without aspirating a blood vessel of the heart wall surface.

Further, the suction head 101 may be formed in a size not less than 5 mm in diameter, preferably not less than 10 mm in diameter in case of a circular plan view shape. On the other hand, a diameter of the suction head 101 may be not more than 60 mm, preferably not more than 50 mm.

Also, in case where the suction head 101 is of a substantially oval shape in a plan view, a length of the major axis may be not less than 20 mm, more preferably not less than 30 mm. On the other hand, a length of the major axis may be not more than 60 mm, preferably not more than 50 mm. Likewise, a length of the minor axis of the suction head 101 may be not less than 5 mm, preferably not less than 10 mm. On the other hand, a length of the minor axis may be not more than 30 mm, preferably not more than 20 mm. In addition, a preferable range of a height of the suction head 101 may be not less than 5 mm to not more than 30 mm.

A suction head 101 formed in the foregoing dimensions can be firmly stuck to a heart surface, and the heart can therefore be securely held. Also, a suction head 101 of such dimensions provides sufficient workability in the procedure, while stably remaining on the heart surface.

Further, it is preferable that the suction head 101 of the instrument for coronary artery bypass graft surgery shown in FIG. 1 is formed a tapered shape having a greater diameter at an end portion of the suction head 101. Such shape prevents the suction head 101 from inwardly deforming because of a suction pressure when making contact with a heart wall under a suctioning condition. Also, dimensions and a shape of a plurality of suction heads 101 may not be necessarily the same. For example, a suction head 101 to be fitted to the apex cordis may be made in largest dimensions. Such arrangement enhances security in retaining a heart at a desired position.

Also, the suction head 101 may be provided with a surface opening at a sticking area thereof. The opening may communicate with the flexible tube 102. Further, a mesh or the like having a plurality of small holes may be additionally provided so as to cover the opening of the suction head 101. In this case, a heart wall surface makes contact with the suction head 101 via the mesh.

Also, a projection may be formed around the opening of the suction head 101, and a mesh may be additionally provided so as to define a gap from the opening. Such structure prevents a decrease of a suction area, thereby improving a suction power of the suction head 101. The mesh or the like may be made of a non-woven cloth of water-absorbing property, cotton or the like.

Figure 4A:
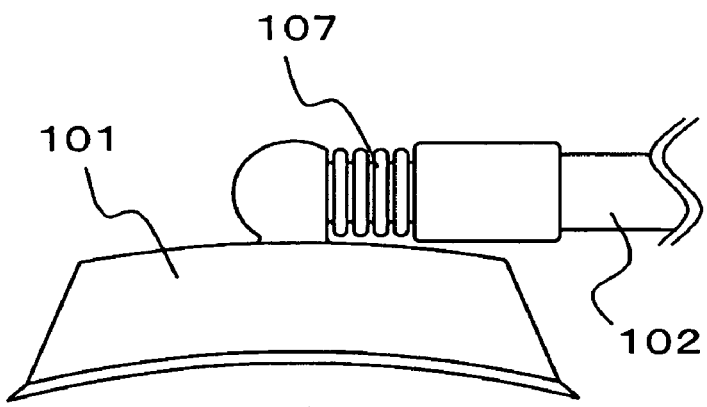
FIGS. 4A to 4E are schematic drawings showing a configuration of a suction head of the instrument for coronary artery bypass graft surgery according to an embodiment of the present invention.
Figure 4B:
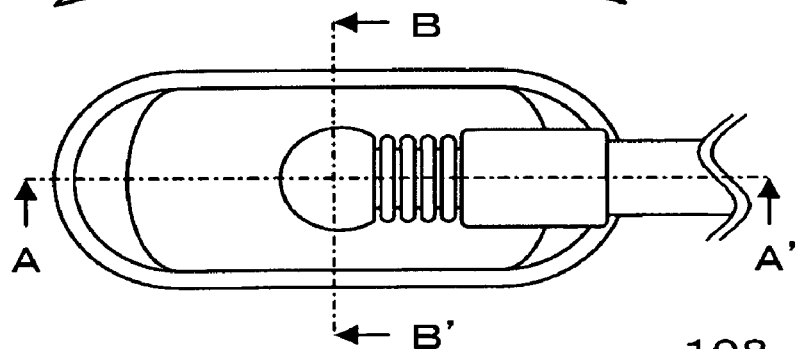
Figure 4C:
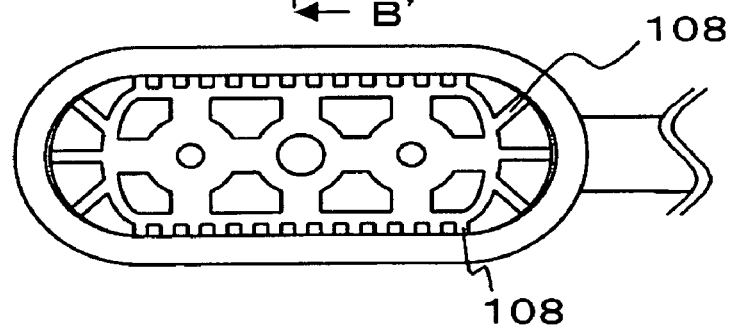
Figure 4D:
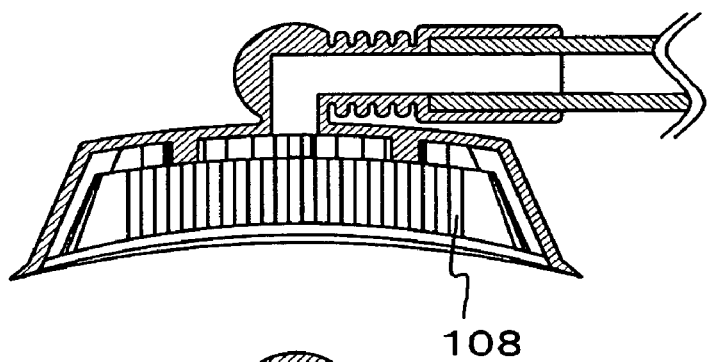
Figure 4E:
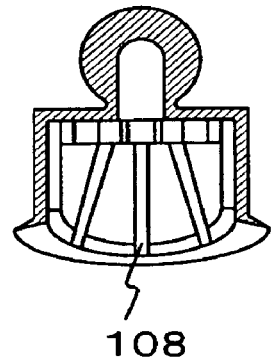

Further, it is preferable that a plurality of slit-like grooves is formed on an inner surface of the opening of the suction head 101. FIGS. 4A to 4E are drawings showing a configuration of the suction head 101 provided with the slits. FIG. 4A is a front view of the suction head 101. FIG. 4B is a plan view of the suction head 101 viewed from an upper position. FIG. 4C is a plan view of the suction head 101 viewed from a lower position. FIG. 4D is a cross-sectional view taken along the line A-A' of FIG. 4B. Finally, FIG. 4E is a cross-sectional view taken along the line B-B' of FIG. 4B.

FIGS. 4A through 4E represent a case where the suction head 101 is of a rectangular shape but with rounded corners. As shown in FIGS. 4C to 4E, the plurality of slit-like grooves, slits 108, may be provided which extend in a substantially orthogonal direction with respect to the sticking area (in other words, along a direction of the suction) and substantially parallel to one another.

Also, the plurality of slits 108 is radially extending from a central portion of the suction head 101 toward a peripheral portion thereof. Accordingly, a liquid inside the suction head 101 can be efficiently drained from inside the opening toward outside. Also, the plurality of slits 108 may be formed in a circumferential direction along an inner surface of the suction head 101. Further, it is preferable that the slits 108 reach the proximity of an edge of the suction head 101. Such configuration permits ensured application of a suction pressure over an entire area of the suction head 101, in addition to the draining effect. As a result, the suction power can be increased.

Forming the slit-like grooves provides a draining effect of body fluid etc. on an organ surface. Accordingly, the suction head 101 can be prevented from laterally slipping on the organ. A preferable width of the slit 108 may be not less than 0.2 mm to not more than 1 mm, and a preferable depth may be not less than 0.5 mm to not more than 5 mm. Such dimensions prevent the organ from entirely intruding into the slit 108 and from resultantly degrading the draining effect of the slit. Therefore, the draining capability of the suction head 101 can be improved.

Figure 5:
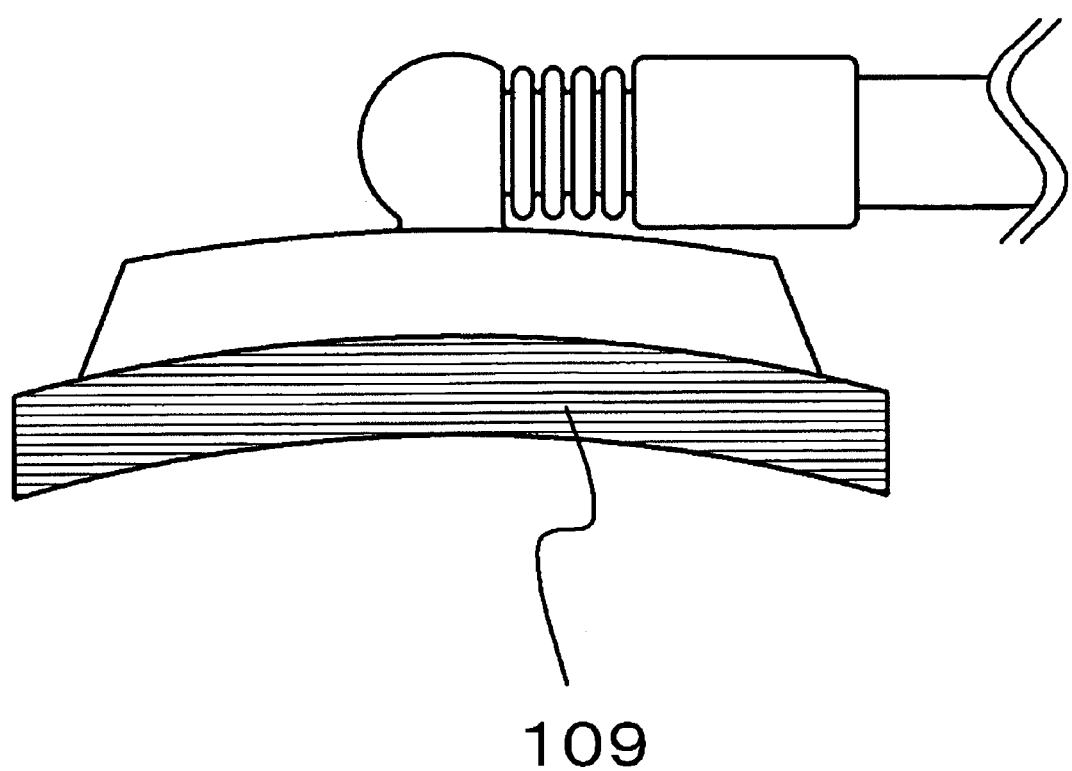
FIG. 5 is a schematic drawing showing a configuration of a suction head of the instrument for coronary artery bypass graft surgery according to another embodiment of the present invention.

Also, in the instrument for coronary artery bypass graft surgery shown in FIG. 1, it is preferable that a soft portion is provided at an edge of the suction head 101. FIG. 5 is a schematic drawing showing a configuration of such suction head 101. Referring to FIG. 5, since a soft material 109 is provided at an edge of the suction head 101, a soft portion is constituted at the edge of the suction head 101. Here, the edge of the suction head 101 is made softer than an inner portion of the suction head 101. Such structure permits the suction head 101 to better follow-up a soft organ, and resultantly enhances the suction power.

Methods of making an end portion of the suction head 101 softer include making the end portion thinner than other portions, attaching a soft material, and so on. Alternatively, a hardness of the end portion may be reduced by 20% or more from a hardness of a main portion of the suction head 101. Examples of such material include the materials cited above for the suction head 101 but having a lower hardness, and an independent foam sponge, a gel material.

Now back to FIG. 1, the instrument for coronary artery bypass graft surgery is provided with a retainer 104 which serves to retain the flexible tube. The retainer 104 controls a position of the suction head 101 and keeps it at a desired or predetermined position. The retainer 104 may be preferably constituted of a material that has a low elongation factor and a high breaking strength. Employing such material for the retainer 104 permits securely controlling the position of the suction head 101 and retaining the suction head 101 at a desired or predetermined position. The retainer 104 may be constituted of a metal such as a stainless steel. Alternatively, a resin material such as a polyamide resin, a polycarbonate resin, a hard vinyl chloride resin, a silicone resin and so forth may be employed.

Further, in the instrument for coronary artery bypass graft surgery shown in FIG. 1, the flexible tube 102 communicating with the plurality of suction heads 101 attached to the heart wall surface and the respective retainers 104 may be fixed to a rib retractor with a pulling forceps or the like. Adjusting a position of the heart with the flexible tube 102 and the retainer 104 fixed to a rib retractor with a pulling forceps or the like permits adjusting the heart position from a plurality of directions, not only from a single direction. Accordingly, the heart can be prevented from shifting its position or falling off from the instrument during an anastomosis procedure. Alternatively, the retainer 104 may be connected to the flexible tube 102 in such a manner that the retainer 104 can slide to a desired position on the flexible tube 102. Such structure allows the retainer 104 to be fixed to the flexible tube 102 at an appropriate position for pulling the retainer 104, thereby improving efficiency in a pulling operation.

Further, in the instrument for coronary artery bypass graft surgery shown in FIG. 1, the three-way cock 103 mounted on the main tube may be closed in advance so that the suction source 106 does not communicate with the sub tubes, and adjusted after fitting the suction head 101 to the heart wall surface to achieve a communication between the suction head 101 and the flexible tube 102, to thereby suction the heart wall via the suction head 101. Also, removal of the suction head 101 from the heart wall may be executed through manipulating the three-way cock 103 to disconnect the communication with the suction source 106 and opening to air.

Also, in the instrument for coronary artery bypass graft surgery shown in FIG. 1, the connector 107 is located between the suction head 101 and the flexible tube 102, for the purpose of connecting them. The connector 107 allows one of the suction head 101 and the flexible tube 102 to relatively move with respect to the other. For example, the flexible tube 102 may be made movable as desired via the connector 107, with respect to the suction head 101. Making the flexible tube 102 movable with respect to the suction head 101 permits absorbing a twisting stress applied when the flexible tube 102 is pulled in a different direction from an initial setting or a stress originating from a pumping motion of the heart, thereby preventing the suction head 101 from falling off from the heart wall surface and thus enhancing safety. The connector 107 may be constituted of a bellows tube for example, so as to allow a free movement of the flexible tube 102 with respect to the suction head 101.

Also, the connector 107 may be designed so that an angular motion range of the flexible tube 102 with respect to the suction head 101 becomes not less than 30 degrees to not more than 180 degrees, in a horizontal plane parallel to a sticking area of the suction head 101. Likewise, the connector 107 may be designed so that an angular motion range of the flexible tube 102 with respect to the suction head 101 becomes not less than 30 degrees to not more than 180 degrees, in a vertical plane perpendicular to a sticking area of the suction head 101. Setting the angular motion range to be not smaller than 30 degrees provides sufficient freedom of motion to the flexible tube 102 with respect to the suction head 101. On the other hand, setting the angular motion range to be not greater than 180 degrees restrains occurrence of kink of the heart wall surface attached the suction head 101 to, thereby enhancing security in holding the heart.

Also, it is preferable that the connector 107 is connected to the proximity of a central portion of the suction head 101 in a plan view. Such configuration permits applying a uniform stress to the suction head 101 when the flexible tube 102 is pulled. Accordingly, the heart can be prevented from being injured while suctioning to the suction head 101. Further, it is preferable that the connector 107 connects the suction head 101 and the flexible tube 102 such that the sticking area of the suction head 101 becomes parallel to an extension of the flexible tube 102. Such configuration prevents the suction head 101 from becoming too bulky, thereby permitting securely fixing the heart within a limited space.

Further, in the instrument for coronary artery bypass graft surgery shown in FIG. 1, a switchgear is mounted on the flexible tube 102. The switchgear may be embodied as the three-way cock 103 as shown in FIG. 1. One or more three-way cocks 103 may be provided on the respective sub tubes and on the main tube. In this way, each of the three-way cocks 103 can be independently manipulated, to thereby individually control the respective suction heads 101.

Further, in case where the three-way cock 103 is serving as the switchgear, a stopper may be provided to delimit a motion range of the cock in two different ways by preventing the cock from rotating in residual one way, such configuration permits:

i) surely applying a suction pressure to the heart wall when attaching the suction head 101 to the heart wall, and ii) surely disconnecting the suction pressure from the suction source 106 and opening to air, when removing the suction head from the heart wall Alternatively, as a system of delimiting a motion of the switchgear in two ways to permit the above effects (i) and (ii), a member which orthogonally slides with respect to the flexible tube 102 may be provided, instead of a rotating cock as the three-way cock 103.

In the instrument for coronary artery bypass graft surgery shown in FIG. 1 is provided with the multiple sets of suction units. In case where one suction unit is provided, since the heart is retained at only a single position the heart can move in a large range. Also, since the instrument utilizes a force in only one direction to hold the heart, the force of the heart against the instrument to go back to an original position is large. Accordingly, the heart may shift from an appropriate position or even fall off from the instrument. In case where multiple sets of suction units are provided, the instrument utilizes forces in multiple directions to hold the heart. Such structure can disperse the force of the heart to go back to an original position, thus to stably retain the heart at a desired position.

Also, in the instrument for coronary artery bypass graft surgery shown in FIG. 1 is provided with at least three sets of suction units. Even though two sets of suction units are provided, still the heart has a freedom of motion in some range. In case where at least three sets of suction units are provided, the heart is held so as to enclose from at least three of directions. And in case where at least three sets of suction units are provided, a sufficient contact area can be secured with a heart wall surface, thus to stably retain the heart at a desired position.

In short, since the instrument for coronary artery bypass graft surgery shown in FIG. 1 is provided with at least three sets of suction units, the instrument can adjust a position of the heart preventing the heart from shifting its position or falling off from the instrument, so that an anastomosis procedure can be safely performed, unlike a conventional instrument which has only two or less suction head.

Still further, providing a plurality of slit-like grooves 108 (FIG. 4) on the suction head 101 prevents the suction head 101 from laterally slipping on an organ surface, and permits ensured application of a suction pressure over an entire area including an end portion of the suction head 101. Accordingly, a suction power of the instrument can be increased. Also, providing a soft material 109 on an edge of the suction head 101 to constitute a softer portion permits the suction head 101 to better follow-up a soft organ, and resultantly enhances the suction power.

Figure 2:
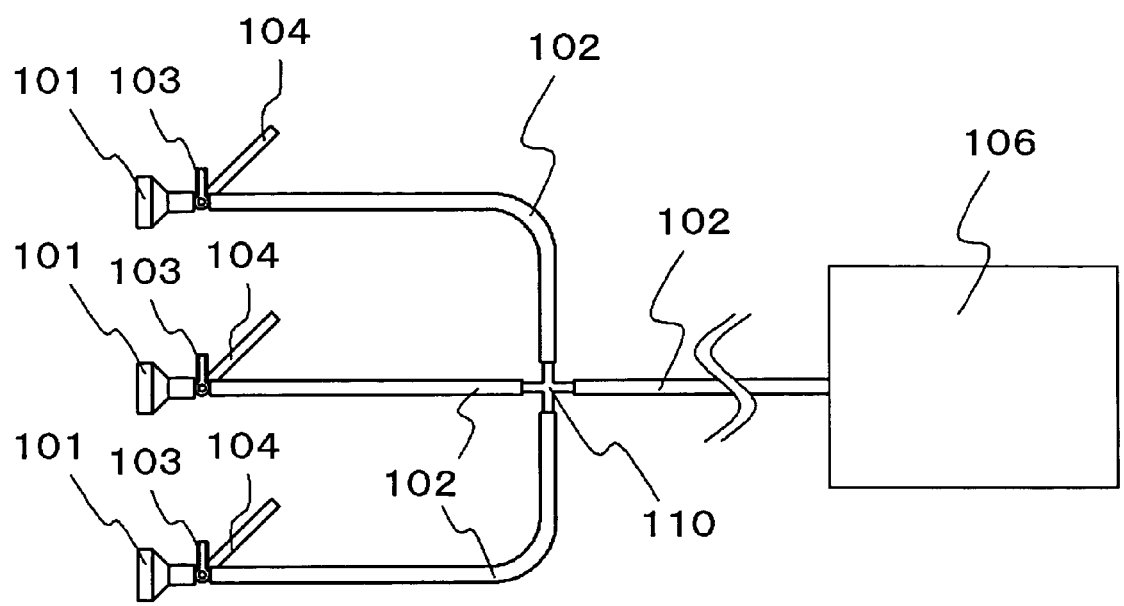
FIG. 2 is a schematic drawing showing a configuration of an instrument for coronary artery bypass graft surgery according to another embodiment of the present invention.
Figure 3:
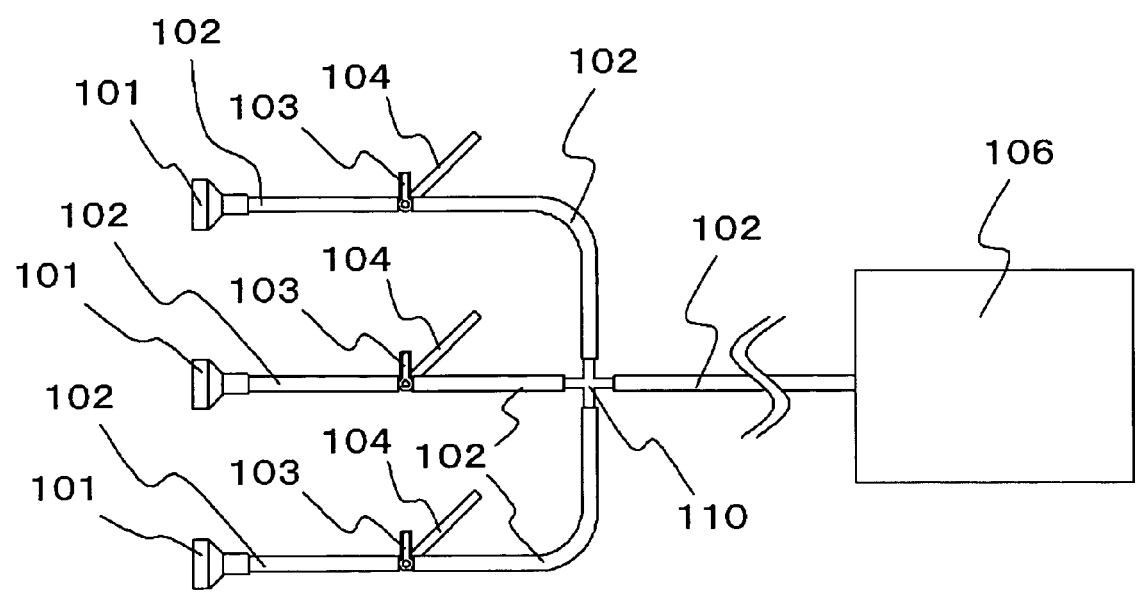
FIG. 3 is a schematic drawing showing a configuration of an instrument for coronary artery bypass graft surgery according to another embodiment of the present invention.

FIGS. 2 and 3 are schematic drawings showing a different configuration of an instrument for coronary artery bypass graft surgery. The structure of the instrument for coronary artery bypass graft surgery shown in FIG. 1 is equally applicable to the instrument of FIGS. 2 and 3. On the contrary, the constitution shown in FIGS. 2 and 3 is equally applicable to the instrument for coronary artery bypass graft surgery of FIG. 1. As shown in FIGS. 2 and 3, a cross joint 110 may be provided in place of the three-way joint 105 shown in FIG. 1.

In the instrument for coronary artery bypass graft surgery shown in FIG. 2, the switchgear is located in the proximity of the suction head 101. Also, the connector 107 is not provided between the suction head 101 and the flexible tube 102. In addition, the sticking area of the suction head 101 is orthogonally fixed with respect to an extension of the flexible tube 102.

A switchgear connected to the suction head 101 and to the flexible tube 102 to serve to achieve a communication between the suction head 101 and the flexible tube 102 may be embodied as a two-way cock or the three-way cock 103 shown in the drawings. Such structure provides significant simplicity in manipulating the instrument for coronary artery bypass graft surgery.

To operate the instrument for coronary artery bypass graft surgery shown in FIG. 2, the two-way cock or the three-way cock 103 is first set so as to disconnect a suction line between the suction source 106 and the flexible tube 102, and hence the suction head 101, and the suction head 101 is fitted to a heart wall surface. Thereafter, the two-way cock or the three-way cock 103 is adjusted to achieve a communication between the suction head 101 and the flexible tube 102. By doing so, the suction head 101 can be stuck to a heart wall. On the contrary, when removing the suction head 101 from the heart wall, the two-way cock or the three-way cock 103 is manipulated to again disconnect the suction line between the suction head 101 and the suction source 106, and opened to air.

Also, the retainer 104 is located close to the suction head 101. The retainer 104 controls a position of the suction head 101. The retainer 104 may be preferably constituted of a material that has a low elongation factor and a high breaking strength. For example, a metal such as a stainless steel or a resin such as a polyamide resin, a polycarbonate resin, a hard vinyl chloride resin, and a silicone resin may be employed. Adjustment of the heart position can be performed by pulling the flexible tube 102 communicating with the three-way cock 103 disposed close to the plurality of suction heads 101 being attached to the heart wall surface, or the respective retainer 104 connected to the flexible tube 102.

In the instrument for coronary artery bypass graft surgery shown in FIG. 2, locating the three-way joint 105 and the retainer 104 in the proximity of the suction head 101 provides increased simplicity in operation to an operator.

Further, in the instrument for coronary artery bypass graft surgery shown in FIG. 3, the three-way cock 103 serving as a switchgear and the retainer 104 are located at a distant position from the suction head 101, unlike the instrument for coronary artery bypass graft surgery of FIG. 2. Disposing the three-way cock 103 and the retainer 104 away from the suction head 101 reduces a bulk around the suction head 101. Accordingly, a position at which to fit the suction head 101 is not restricted even when there is only a small gap between the heart and a pericardium around the heart.

Further, in the instrument for coronary artery bypass graft surgery shown in FIG. 2 and FIG. 3, the flexible tube 102 communicating with the plurality of suction heads 101 attached to the heart wall surface and the respective retainers 104 connected to the three-way cock 103 serving as a switchgear may be fixed to a rib retractor with a pulling forceps or the like.

Although the present invention has been described by way of exemplary embodiments along with the accompanying drawings, it should be understood that many changes and substitutions may further be made by those skilled in the art without departing from the scope of the present invention which is defined by the appended claims.

For example, while the surgical instruments for coronary artery bypass graft described in the foregoing embodiments are provided with three suction heads 101 connecting to a single suction source 106, the number of the suction heads 101 may be different as long as it is three or more. Accordingly, four or more suction heads may be provided with respect to one suction source.

Also, while the surgical instruments for coronary artery bypass graft described in the foregoing embodiments are provided with a trap between the suction source 106 and the suction units where into blood, body fluid, or cleaning fluid and the like is trapped.

The instrument for coronary artery bypass graft surgery according to the present invention can adjust a position of a heart preventing the heart from shifting its position or falling off from the instrument, when handling an affected part that is difficult to perform an anastomosis in OPCAB surgery, thereby facilitating a safe anastomosis.

What is claimed is:

1. A surgical instrument for coronary artery bypass graft surgery comprising:
   at least three sets of suction units, each of such sets being respectively provided with a flexible tube;
   a single suction head disposed at an end portion of each said flexible tube;
   a connector disposed between said suction head and said flexible tube, which connector is provided with a bellows tube communicating with said flexible tube and
   each suction head having a sticking area with a single opening on said sticking area, said opening having a plurality of slit-like grooves formed on an inner surface thereof, and each said single opening being in communication with a said flexible tube;
   i) the slit-like grooves extending in a substantially orthogonal direction with respect to the sticking area and being substantially parallel to each other;
   the plurality of slit-like grooves radially extending from a central portion of each suction head towards a peripheral portion thereof;
   the slit-like grooves reaching a proximity of an edge of each suction head; and
   ii) the slit-like grooves are constituted such that a liquid inside the suction head is drained from inside the opening towards outside;
   a switchgear mounted on each said flexible tube; and
   a retainer mounted on each said flexible tube which retains said flexible tube.

2. The surgical instrument as set forth in claim 1, wherein said connector allows one of said suction head and said flexible tube to relatively move with respect to the other.

3. The surgical instrument as set forth in claim 2, wherein an angular motion range of said flexible tube with respect to said suction head is not less than 30 degrees to not more than 180 degrees, in a horizontal plane parallel to a sticking area of said suction head.

4. The surgical instrument as set forth in claim 2, wherein an angular motion range of said flexible tube with respect to said suction head is not less than 30 degrees to not more than 180 degrees, in a vertical plane perpendicular to a sticking area of said suction head.

5. The surgical instrument as set forth in claim 1, wherein an end portion of said suction head is made softer than an inner portion of said suction head.

6. The surgical instrument as set forth in claim 1, wherein said flexible tube includes a main tube, a branch section communicating with said main tube, and a plurality of sub tubes respectively communicating with said branch section, such that a plurality of said suction heads are respectively disposed on each of said sub tubes.

7. The surgical instrument as set forth in claim 1, wherein a plurality of said suction heads are connected to a single suction source via said flexible tube.

8. The surgical instrument as set forth in claim 1 wherein each suction head is disposed to ensure application of suction pressure over entire area of the suction head.

9. A surgical instrument for coronary artery bypass graft surgery comprising:
   at least three sets of suction units, each of such sets being respectively provided with a flexible tube;
   a single suction head disposed at an end portion of each said flexible tube to ensure application of suction pressure over entire area of the suction head;
   a switchgear mounted on each said flexible tube; and
   a retainer mounted on each said flexible tube which retains said flexible tube
   wherein said suction head having a sticking area is provided with a single opening on said sticking area, said opening having a plurality of slit-like grooves formed on an inner surface thereof;
   iii) the slit-like grooves extending in a substantially orthogonal direction with respect to the sticking area and being substantially parallel to each other;
   the plurality of slit-like grooves radially extending from a central portion of each suction head towards a peripheral portion thereof;
   the slit-like grooves reaching a proximity of an edge of each suction head; and
   iv) the slit-like grooves are constituted such that a liquid inside the suction head is drained from inside the opening towards outside.

10. The surgical instrument as set forth in claim 9, wherein the suction heads are of rectangular shape with rounded corners.

11. A surgical instrument for coronary artery bypass graft surgery comprising:
   at least three sets of suction units, each of such sets being respectively provided with a flexible tube;
   a single suction head disposed at an end portion of each said flexible tube;
   a connector disposed between said suction head and said flexible tube, which connector is provided with a bellows tube communicating with said flexible tube so as to allow free movement of the flexible tube with respect to the suction head; and
   each suction head having a sticking area with a single opening on said sticking area, said opening having a plurality of slit-like grooves formed on an inner surface thereof, and each said single opening being in communication with a said flexible tube;
   i) the slit-like grooves extending in a substantially orthogonal direction with respect to the sticking area and being substantially parallel to each other;
   the plurality of slit-like grooves radially extending from a central portion of each suction head towards a peripheral portion thereof;
   the slit-like grooves reaching a proximity of an edge of each suction head; and
   ii) the slit-like grooves are constituted such that a liquid inside the suction head is drained from inside the opening towards outside;
   a switchgear mounted on each said flexible tube; and
   a retainer mounted on each said flexible tube which retains said flexible tube.

* * * * *